United States Patent
Heeren

(10) Patent No.: US 10,137,034 B2
(45) Date of Patent: Nov. 27, 2018

(54) PRESSURE-SENSING VITRECTOMY SURGICAL SYSTEMS AND METHODS

(71) Applicant: Novartis AG, Basel (CH)

(72) Inventor: Tammo Heeren, Aliso Viejo, CA (US)

(73) Assignee: Novartis AG, Basel (CH)

( * ) Notice: Subject to any disclaimer, the term of this patent is extended or adjusted under 35 U.S.C. 154(b) by 355 days.

(21) Appl. No.: 14/090,360

(22) Filed: Nov. 26, 2013

(65) Prior Publication Data

US 2015/0148836 A1    May 28, 2015

(51) Int. Cl.
| | | |
|---|---|---|
| *A61F 9/00* | (2006.01) | |
| *A61F 9/007* | (2006.01) | |
| *A61M 3/02* | (2006.01) | |
| *A61M 1/00* | (2006.01) | |
| *A61B 3/16* | (2006.01) | |

(52) U.S. Cl.
CPC ............ *A61F 9/00781* (2013.01); *A61B 3/16* (2013.01); *A61F 9/00763* (2013.01); *A61M 1/0039* (2013.01); *A61M 3/0258* (2013.01); *A61M 3/0279* (2013.01); *A61M 2205/3344* (2013.01)

(58) Field of Classification Search
CPC .. A61F 9/00781; A61F 9/00763; A61F 9/007; A61M 3/00258; A61M 1/0039; A61M 3/0279; A61M 2205/3344
See application file for complete search history.

(56) References Cited

U.S. PATENT DOCUMENTS

| | | | |
|---|---|---|---|
| 4,548,205 A | | 10/1985 | Armeniades et al. |
| 4,722,350 A | * | 2/1988 | Armeniades ............ A61B 3/16 600/398 |
| 5,865,764 A | * | 2/1999 | Moorhead ................ A61B 5/03 600/561 |
| 6,059,792 A | * | 5/2000 | Josephberg ......... A61F 9/00763 604/22 |
| 6,491,661 B1 | | 12/2002 | Boukhny et al. |
| 6,743,245 B2 | | 6/2004 | Lobdell |
| 7,393,189 B2 | | 7/2008 | Davis et al. |
| 7,644,603 B2 | | 1/2010 | Gordon et al. |
| 7,648,465 B2 | | 1/2010 | Gordon |

(Continued)

FOREIGN PATENT DOCUMENTS

| | | |
|---|---|---|
| CN | 1033737 A | 7/1989 |
| EP | 0 482 858 A2 | 4/1992 |

(Continued)

OTHER PUBLICATIONS

International Search Report and Written Opinion issued for PCT/US2014/064423 dated Feb. 9, 2015, 11 pgs.

*Primary Examiner* — Kathleen Holwerda
*Assistant Examiner* — Christina Lauer

(57) ABSTRACT

A vitrectomy surgical system is disclosed herein. The surgical system includes a vitrectomy probe having a cutting portion comprising an inner cutting tube, an outer cutting tube, and an outer port. The inner cutting tube is movable relative to the outer cutting tube to cut vitreous humor during a vitrectomy procedure. The surgical system further includes a motor configured to move the inner cutting tube relative to the outer cutting tube and one or more pressure sensors coupled to the vitrectomy probe to measure a pressure proximate to a distal portion of the vitrectomy probe and provide pressure feedback. Related systems and methods are also included.

20 Claims, 5 Drawing Sheets

(56) References Cited

U.S. PATENT DOCUMENTS

| | | |
|---|---|---|
| 8,246,580 B2 | 8/2012 | Hopkins et al. |
| 8,287,486 B2 * | 10/2012 | Injev ................... A61F 9/00745 |
| | | 604/22 |
| 8,465,467 B2 | 6/2013 | Gao |
| 8,608,681 B2 | 12/2013 | Injev |
| 8,876,751 B2 | 11/2014 | Dacquay et al. |
| 9,119,699 B2 | 9/2015 | Gordon |
| 9,119,701 B2 | 9/2015 | Gordon |
| 2001/0016707 A1 | 8/2001 | Urich et al. |
| 2011/0034864 A1 * | 2/2011 | Dacquay ............. A61M 1/0031 |
| | | 604/28 |
| 2011/0137231 A1 | 6/2011 | Sorensen et al. |
| 2011/0295191 A1 | 12/2011 | Injev |
| 2012/0158030 A1 | 6/2012 | Underwood et al. |
| 2013/0150782 A1 | 6/2013 | Sorensen et al. |
| 2014/0163455 A1 | 6/2014 | Wilson et al. |
| 2014/0323953 A1 | 10/2014 | Sorensen et al. |
| 2015/0173948 A1 | 6/2015 | Heeren |

FOREIGN PATENT DOCUMENTS

| | | |
|---|---|---|
| EP | 1225854 A1 | 7/2002 |
| JP | 1989207059 A | 8/1989 |
| JP | 1991049756 A | 3/1991 |
| WO | 9825515 A1 | 6/1998 |
| WO | WO 02/26016 A2 | 4/2002 |

\* cited by examiner

PRESSURE-SENSING VITRECTOMY SURGICAL SYSTEMS AND METHODS

BACKGROUND

The present invention pertains to vitrectomy probes, systems, and methods. More particularly, but not by way of limitation, the present invention pertains to the monitoring of vitrectomy probes and their operating environments.

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. These cutting probes typically include a hollow outer cutting member, a hollow inner cutting member arranged coaxially with and movably disposed within the hollow outer cutting member, and a port extending radially through the outer cutting member near the distal end thereof. Vitreous humor and/or membranes are aspirated into the open port, and the inner member is actuated, closing the port. Upon the closing of the port, cutting surfaces on both the inner and outer cutting members cooperate to cut the vitreous and/or membranes, and the cut tissue is then aspirated away through the inner cutting member.

Many complications can arise during procedures requiring the use of these microsurgical cutting probes. Some of these complications may arise because of the nature of the procedures. For example, during removal of vitreous humor, the eye may collapse if the pressure in the vitreous chamber is allowed to drop too much. Additionally, complication may arise with the cutting probes themselves. For example, if the pneumatic line of the cutting probe or an infusion line becomes kinked or nearly kinked, maintaining consistent control of the probe may become difficult as the pressure fluctuates.

The present disclosure is directed to addressing one or more of the deficiencies in the prior art.

SUMMARY

In one exemplary aspect, the present disclosure is directed to a system for providing irrigation into an eye of a patient during a medical procedure. The system includes an infusion line configured to place a fluid source in fluid communication with an eye of the patient and one or more pressure sensors coupled to the infusion line and configured to measure a pressure about the infusion line during the medical procedure. The infusion line includes a relatively more flexible elongate member having a proximal end, a distal end, and a lumen extending therethrough from the proximal end to the distal end. The lumen is configured to pass irrigation fluid to the eye of the patient. The infusion line further includes a relatively more rigid engagement member at the distal end that is configured to penetrate into a vitreous chamber of the eye of the patient.

In an additional exemplary aspect, the present disclosure is directed to a vitrectomy surgical system. The system includes a vitrectomy probe having a cutting portion that has an inner cutting tube, an outer cutting tube, and an outer port. The inner cutting tube is movable relative to the outer cutting tube to cut vitreous humor during a vitrectomy procedure. The system also includes a motor configured to move the inner cutting tube relative to the outer cutting tube to open and close the outer port and one or more pressure sensors coupled to the vitrectomy probe to measure a pressure proximate to a distal portion of the vitrectomy probe and provide pressure feedback.

In another exemplary aspect, the present disclosure is directed to a method of treating an ophthalmic condition. The method comprising inserting a probe, including at least one pressure sensor, through a sclera into a vitreous chamber of a patient, measuring a vitreous chamber pressure with the at least one pressure sensor to provide a vitreous chamber pressure measurement, and adjusting a parameter of a vitreous humor removal procedure based upon the vitreous chamber pressure measurement.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the devices and methods disclosed herein and together with the description, serve to explain the principles of the present disclosure.

Figure 1:
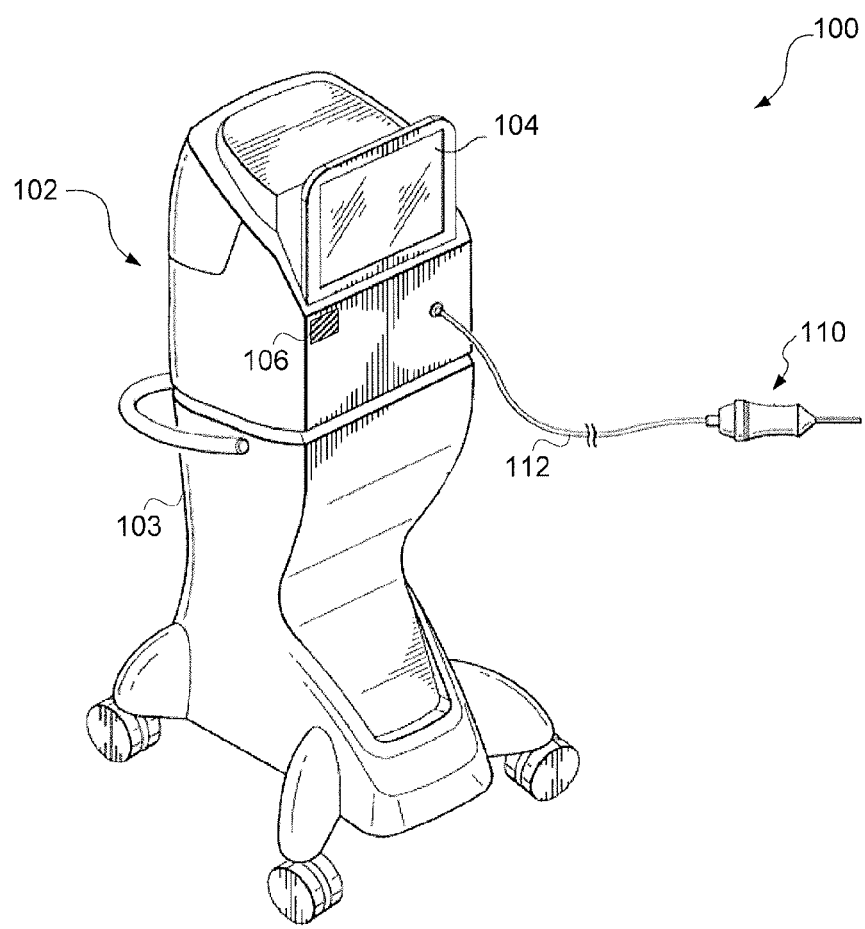
FIG. 1 is an illustration of a surgical system according to exemplary aspects of the present disclosure.

These figures will be better understood by reference to the following detailed description.

DETAILED DESCRIPTION

For the purposes of promoting an understanding of the principles of the present disclosure, reference will now be made to the embodiments illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to systems and methods for monitoring pressure at various points of interest during ophthalmic surgery, particularly surgeries in which the surgeon needs to remove vitreous humor from a patient's eye. Pressure changes and excessively low or high pressures can complicate the performance of such procedures, putting the patient at risk. In some aspects described herein, a vitrectomy probe includes pressure sensors to monitor an intraocular pressure, a pressure inside the probe tip, and an ambient pressure. In some additional aspects described herein, an infusion line includes pressure sensors along its length to identify and locate kinks in the line. The systems and methods disclosed herein may enable a surgeon to better monitor important pressures and to react quickly to pressure drops that arise during a procedure. By improving the surgeon's abilities or by enabling the system to respond to pressure conditions during a vitrectomy procedure, outcomes for patients may be improved.

FIG. 1 illustrates a vitrectomy surgical system 100 according to an exemplary embodiment. The surgical system 100 includes a console 102 that has mobile base housing 103 and an associated display screen 104 showing data relating to system operation and performance during a vitrectomy surgical procedure. The surgical system 100 includes a vitrectomy probe system 110 that will be described in greater detail below. The console 102 of the surgical system 100 includes features that may allow for control of the vitrectomy probe system 110. For example pneumatic and/or electrical supply lines 102 may couple the probe system 110 to the housing 102. The supply lines 102 facilitate control and monitoring to the probe system 110 by also transmitting data between the probe system 110 and the console 102. The console 102 further includes one or more processors in communication with a memory having computer-instructions to control the probe system 110, display information on the screen 104, and receive and process input commands and data. The surgical system 100 may include a network interface for communication with a network. These features facilitate control and monitoring of the probe system 110 during operation. Additionally, these features may facilitate the monitoring, data processing, and control for one or more pressure sensors disposed on or about the probe system 110. Some embodiments of the surgical system 100 further include a pressure sensor 106 disposed on or about the housing 103 to sense an ambient pressure. This ambient pressure may be atmospheric pressure.

Figure 2:
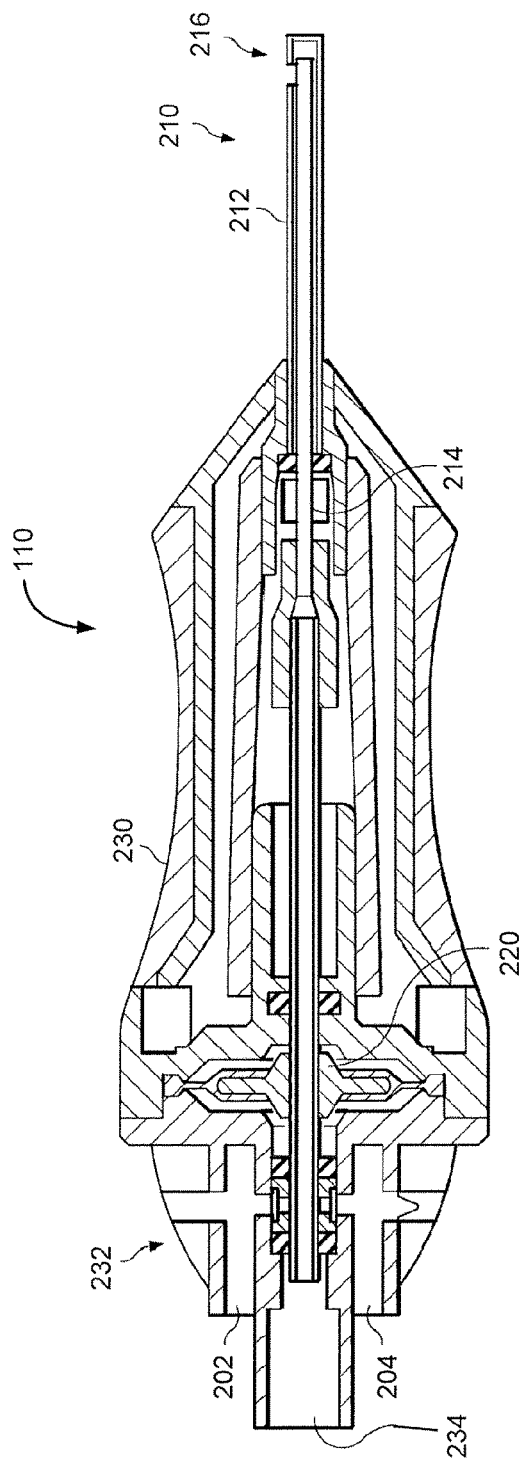
FIG. 2 is a cross-sectional illustration of a vitrectomy probe according to exemplary aspects of the present disclosure.

FIG. 2 shows a cross-sectional view of the vitrectomy probe system 110 previously shown in FIG. 1. In this example, the probe system 110 is a pneumatically driven system that operates by receiving pneumatic pressure alternating through first and second ports 202 and 204 over the supply lines 112 illustrated in FIG. 1. The probe system 110 includes as its basic components a cutter 210 and a probe actuator shown here as a reciprocating air driven diaphragm 220, all partially encased by a probe housing 230. The probe housing 230 includes an end piece 232 at the probe proximal end with the first and second air supply ports 202, 204 and one suction port 234. The cutter 210 comprises an outer cutting tube 212 and an inner cutting tube 214. As can be seen, the cutter 210 extends from the housing 230 and includes a distal portion 216.

Figure 3:
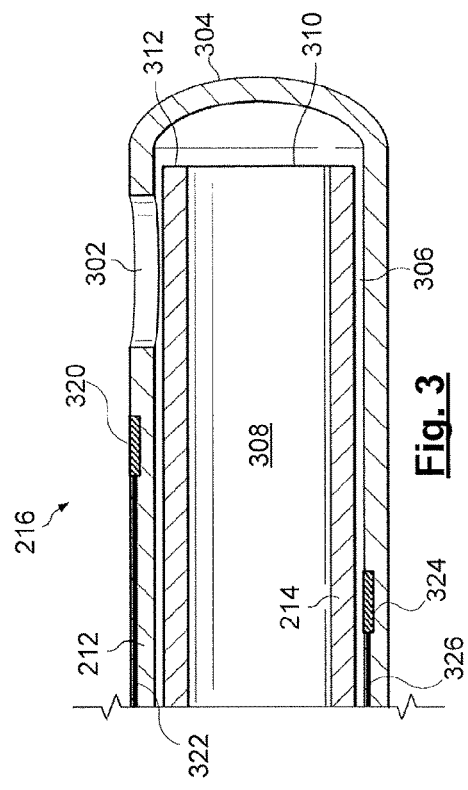
FIG. 3 is a close-up cross-sectional illustration of a distal portion of the cutter of the vitrectomy probe of FIG. 2 according to exemplary aspects of the present disclosure.

FIG. 3 is a cross-sectional view that provides additional detail regarding the distal portion 216 of the cutter 210 as seen in FIG. 2 and discussed above. The distal portion 216 includes an outer port 302 that receives tissue, such as ophthalmic tissue, during use. The outer port 302 is offset from a closed end 304 of the distal portion 216. The outer port 302 is in fluid communication with an inner channel 306 of the outer cutting tube 212. The inner cutting tube 214 is located within the inner channel 306 of the outer cutting tube 212. The inner cutting tube 214 has an inner bore 308, an open end 310, and a cutting surface 312. The inner bore 308 is in fluid communication with an aspiration line coupled to the suction port 234 of FIG. 2. The aspiration line is part of the supply lines 112 of FIG. 1. The suction port 234 connects the aspiration line to a vacuum (providing an aspiration pressure), which may be provided by console 102 or another device, and is used to pull tissue into the outer port 302 when the inner cutting surface 312 is located away from the port 302. The inner cutting tube 214 moves within the inner channel 306 of the outer cutting tube 212 to cut tissue that is pulled into the outer port 302 by the aspiration line. The ophthalmic tissue received by the outer port 302 may include vitreous or membranes.

When used to cut tissue, the inner cutting tube 214 is initially moved away from the outer port 302 and the vacuum pressure pulls tissue into the port 302 and the inner channel 306. The inner cutting tube 214 then moves toward the outer port 302 and severs the tissue within the inner channel 306 with the cutting surface 312. The severed tissue is pulled through the inner bore 308 of the inner cutting tube 214 by the aspiration system. The inner cutting tube 214 then moves away from the outer port 302, and the cutting process is repeated.

With reference now to both FIGS. 2 and 3, the inner cutting tube 214 is driven by air pressure directed on opposing sides of the diaphragm 220. In one example of operation, if air pressure is increased at the first port 202, the diaphragm 220 will move distally, displacing the inner cutting tube 214 relative to the outer cutting tube 212, thereby closing the tissue-receiving outer port 302 of the outer cutting tube 212. This cuts any vitreous material which may have been aspirated into the tissue-receiving outer port 302. Venting the pressure at the first port 202 and increasing the pressure at the second port 204 will move the diaphragm 220 proximally, opening the tissue-receiving outer port 302 so that it can draw in new vitreous material to be cut. It's worth noting that other embodiments include alternative probe actuators. For example, some actuator embodiments include a piston motor in place of a diaphragm. In this type of embodiment, the cutter 210 is arranged so that movement of the piston also moves the inner cutting tube 214 of the cutter 210. Yet other actuator embodiments include other types of pneumatic or electric motors that drive the inner cutting tube 214.

The vitrectomy probe system 110 as depicted in FIGS. 2 and 3, further includes a plurality of pressure sensors. A first pressure sensor 320 is connected to (e.g., embedded in) the outer cutting tube 212 and is configured to sense and measure a pressure outside the outer cutting tube 212. In the illustrated embodiment, the pressure sensor is configured between the outer port 302 and the system housing 230. In other embodiments, the pressure sensor 320 may be positioned on an outer surface of the closed end 304. In general, the pressure sensor 320 is positioned on an outer surface of the outer cutting tube 212 in order to measure the pressure external to the tube 212. This external pressure may be an ambient or atmospheric pressure or may be a pressure within the vitreous chamber, and may be used to determine an intraocular pressure, depending on the positioning of the sensor 320 and the cutter 210. As depicted, the pressure sensor 320 is a fiber optic pressure sensor coupled to electronics in the probe housing 230 as seen in FIG. 2 and/or the console 102 as seen in FIG. 1 by a sensor line 322. The sensor line 322 may be an electrical or a fiber optic line depending on the type of pressure sensor used for pressure sensor 320. Both the pressure sensor 320 and the sensor line 322 are positioned within recesses formed in the outer cutting tube 212 so that the surface of the outer cutting tube 212 remains flush. In some embodiments this recess is formed on the outside of the cutting tube 212, while in others it is formed on the inside, with an opening provided for the sensor 320 to access the external pressure.

A second pressure sensor 324 is included in the cutter 210 so as to measure a pressure internal to the outer cutting tube 212 of the cutter 210. As illustrated, the second pressure sensor 324 is positioned on an inner surface of the outer cutting tube 212. A second sensor line 326 couples the second pressure sensor 324 to electronics as discussed above in connection with the pressure sensor 320. In some embodiments, the pressure sensor 324 may be disposed within the walls of the inner cutting tube 214, either on an outer surface or the inner surface. The pressure sensor 324 permits measurement of pressure within the cutter 210. Use of the pressure sensors 320 and 324 permits a determination of a differential pressure. The pressure sensors 320 and 324 may both be fiber optic pressure sensor in an embodiment, while in other embodiments, other types of pressure sensors are used.

Figure 4:
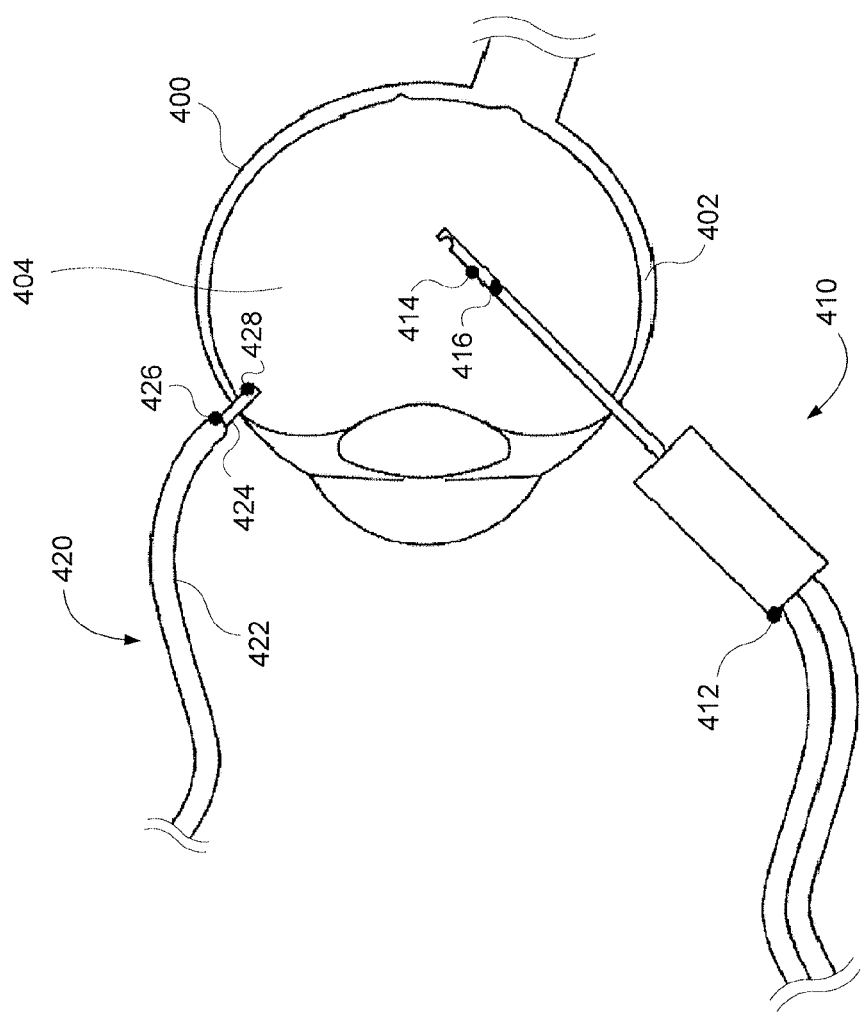
FIG. 4 is an illustration of a vitrectomy probe and an infusion line in situ in an eye according to exemplary aspects of the present disclosure.

FIG. 4 illustrates a partially cross-sectional view of an eye 400 undergoing a procedure involving a vitrectomy probe system 410 and an infusion line or infusion cannula 420. Both the probe system 410 and the infusion line 420 may be coupled to a console, like console 102 of FIG. 1. In FIG. 4, the probe system 410 and the infusion line 420 are inserted through the sclera 402 and into the vitreous chamber 404 of the eye 400. The infusion line 420 is a specialized type of probe used to deliver replacement fluid or irrigation fluid into the vitreous chamber 404 during vitrectomy procedures. A pressure level of the irrigation fluid may be increased or decreased by a surgical system. The probe system 410 is similar to the vitrectomy probe system 110 as depicted in FIGS. 1, 2, and 3. In the illustrated embodiment, the probe system 410 includes a plurality of pressure sensors, including a pressure sensor 412, a pressure sensor 414, and a pressure sensor 416. Each of the pressure sensors 412-416 measures a pressure in a different location. As depicted, the pressure sensor 412 is configured on a housing of the probe system 410 to measure an ambient or atmospheric pressure. As discussed above in connection with FIG. 1, in some embodiments an ambient pressure sensor, like the pressure sensor 412, is provided on an exterior surface of the console 102 coupled electrically and/or pneumatically to the probe system 410.

The pressure sensors 414 and 416 are disposed on a cutter of the probe system 410. These pressure sensors are similar to the pressure sensors 320 and 324 illustrated in FIG. 3. As depicted, the pressure sensor 414 is disposed on the probe system 410 so as to measure the pressure outside of the cutter, i.e. the pressure within the vitreous chamber 404. The pressure sensor 416 is disposed within the cutter so as to measure an internal pressure, i.e. internal to the cutter, that may be used to characterize the vacuum supplied through an aspiration line to the probe system 410. In addition to their respectively sensed pressures, pressure sensors 414 and 416, along with pressure sensor 412, may be used in conjunction to provide a differential pressure, such as a pressure representative of intraocular pressure. The pressures that may be sensed by the probe system 410 facilitate improved control by the surgical system 100 of FIG. 1 by providing additional information that can be processed by the surgical system 100 and used for automated flow and pressure control. For example, by measuring and determining the intraocular pressure of the eye 400 the surgical system 100 may be able to avoid the collapse of the eye 400 due to excessive removal of vitreous humor from the vitreous chamber 404 or the inadequate replacement of the vitreous humor with saline or another appropriate replacement fluid through the infusion line 420 during a vitrectomy procedure by increasing the flow rate of replacement fluid, decreasing the aspiration pressure or the cutting rate, or adjusting these and other parameters. Also, the internal pressure or differential pressure may provide the surgical system data regarding the performance of the probe system 410 in removing vitreous humor.

The differential pressure may be used to define an intraocular pressure. Generally, intraocular pressure, or IOP, is a gauge pressure reading determined by the difference between the absolute pressure in the eye (as measured by the sensor 414) and atmospheric pressure (as measured by the sensor 412). Therefore, in some exemplary embodiments, pressure readings are taken by sensors 412 and 414 simultaneously or nearly simultaneously so that the actual intraocular pressure can be calculated as a function of the measured pressures.

The infusion line 420 comprises a flexible elongate member 422 having a more rigid engagement member 424 affixed at a distal end. The infusion line 420 provides a replacement fluid from a fluid source, carried through a central lumen, in order to maintain an appropriate intraocular pressure as portions of the vitreous humor 404 are removed. As depicted, the infusion line 420 also includes a plurality of pressure sensors including a pressure sensor 426 and a pressure sensor 428. The pressure sensor 426 is disposed on the infusion line 420 so that it remains outside the eye 400 during a surgical procedure. While the pressure sensor 426 is disposed outside the eye 400, the pressure sensor 428 is disposed on a distal portion of the rigid engagement member 424 so as to sense an internal eye pressure that may be used to determine the intraocular pressure during the surgical procedure. As with the pressure sensors 412, 414, and 416 of the probe system 410, the pressure sensors 426 and 428 are fiber-optic pressure sensors in the illustrated embodiment. The rigid engagement member 424 also has a lumen running therethrough, through which the replacement fluid flows to the vitreous chamber 404.

As illustrated in FIG. 4, some embodiments may include redundant pressure sensors. For example, the pressure sensor 428 of the infusion line of 420 may be considered redundant due to the presence of the pressure sensor 414 of the probe system 410. In some embodiments, only one pressure sensor to measure an internal eye pressure may be provided by the combined use of the probe system 410 and the infusion line 420, such that either the probe system 410 or the infusion line 420 includes a pressure sensor within the vitreous chamber 404. Similarly, in some embodiments only one ambient pressure sensor is present. In other embodiments, data for a single pressure is obtained using multiple pressure sensors. The data from each pressure sensor may be provided directly or a mathematical combination of the pressure sensors may be used to provide a single value. Using the pressure measurements obtained from the pressure sensors depicted in FIG. 4 may allow a surgeon to exercise more informed control of probe system 410 and the infusion line 420 during a surgical procedure.

Figure 5:
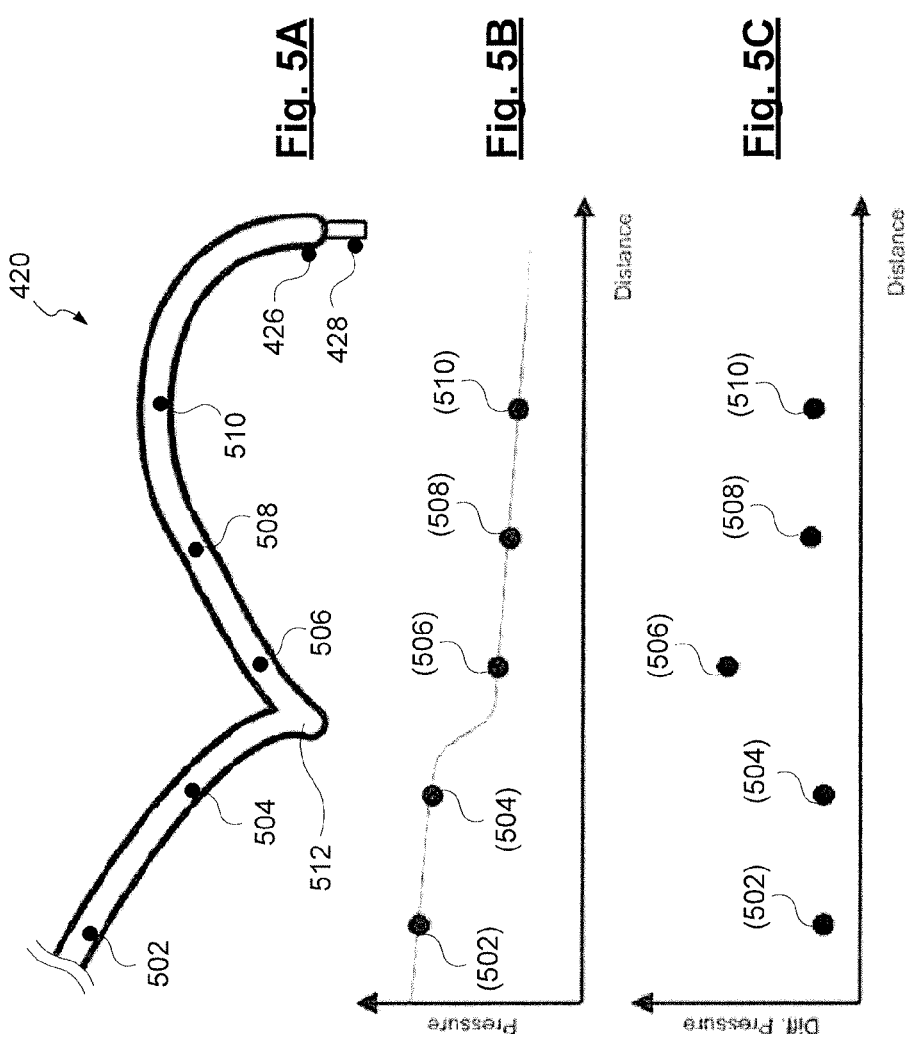
FIG. 5A is an illustration of an infusion line according to exemplary aspects of the present disclosure.
FIGS. 5B and 5C are charts illustrating the relationship of between pressures and along a length of the infusion line of FIG. 5A.

FIG. 5A is an additional illustration of the infusion line 420 previously depicted in FIG. 4. As described earlier, the infusion line 420 comprises a relatively more flexible elongate member 422 with a relatively more rigid engagement member 424 affixed at a distal end thereof. As described above, the infusion line 420 is used to provide a replacement fluid as vitreous humor is removed from an eye during a surgical procedure. As illustrated in FIG. 5A, the infusion line 420 includes pressure sensors 426 and 428, also discussed earlier. In addition to the pressure sensors 426 and 428, the infusion line 420 further includes a plurality of internal pressure sensors distributed along the length of the flexible elongate member 422. As illustrated, these internal pressure sensors include pressure sensors 502, 504, 506, 508, and 510. Other embodiments may include more or fewer pressure sensors. The pressure sensors 502-510 are disposed on or within an inside surface of the flexible elongate member 422, such that they do not impede the flow of the replacement liquid to the eye of a patient undergoing a surgical procedure. While pressure sensors 502-510 are fiber optics pressure sensors as depicted, in other embodiments other types of pressure sensors may be used. Electrical and/or optical supply lines (present but not explicitly depicted in FIGS. 4 and 5A) extend the length of the infusion line 420 to provide power and communication to and from the pressure sensors.

The pressure sensors are positioned within recesses formed in the flexible elongate member 422. The recesses may be formed on an inside or an outside surface of the flexible elongate member 422. Whether formed on the inside or outside surface, the pressure sensors have access through a plurality of associated openings in the lumen running through the flexible elongate member 422, which carries the replacement fluid. For example, each recess is formed as a cutout in the inner surface of the tube inner wall. In some embodiments, the recess is sized to receive the pressure sensor so that the pressure sensor lies flush with the inner wall. In this condition, the pressure sensor may have minimal impact on flow through the lumen. In other embodiments, the recess is less than a thickness of the sensor or more than the thickness of the sensor. The recess may be square shaped or any other shape suitable for receiving and housing the pressure sensor. Elongated recesses are provided for the electrical and/or optical supply lines. When fiber optic pressure sensors are used, a fiber-optic coupling element is provided at a proximal end of the infusion line to communicatively couple the optical supply lines from the pressure sensors to a data processing console, like console 102. In some embodiments, electric coupling elements are used along with electrical pressure sensors such as piezoelectric pressure sensors or microelectromechanical system (MEMS) pressure sensors to monitor and communicate the pressure at points of interest.

In the depicted infusion line 420, the pressure sensors are evenly spaced apart along the length of the flexible elongate member 422. The spacing between individual pressure sensor may be in the range of about 2 inches to about 5 inches. In some embodiments, the spacing may be in the range of about 2 to about 36 inches. The regular, even spacings of the pressure sensors may allow for the detection, by a console such as console 102 of FIG. 1, of a location of a flow problem, such as an obstruction, during use of the infusion line 420. This may be done by identifying pressure differences along the length of the infusion line 420. In general, a pressure drop across the infusion line 420 is equal to the difference in pressures measured at the most proximal and the most distal sensors. Thus, a total pressure drop within the infusion line 420 may be calculated as the pressure measured by sensor 502 minus the pressure measured by sensor 510. Some amounts of pressure loss from sensor 502 to sensor 510 may be tolerable or expected. To identify problematic pressure fluctuations, a threshold pressure change may be used such that if the magnitude of the change measured between any two pressure sensors, adjacent or separated, equals or exceeds the threshold pressure change, a notification is triggered.

For example, during a procedure in which the infusion line 420 is used to provide replacement fluid, the flexible elongate member 422 may become twisted, kinked, or otherwise undesirably positioned so as to partially or completely impede the flow of the replacement fluid into the vitreous chamber of an eye. As illustrated, the flexible elongate member 422 has a kink 512 situated between the locations of pressure sensors 504 and 506. Such instances may cause harmfully low pressures within the eye, posing a danger of collapse. When the flow is temporarily impeded and then restored, an associated pressure spike can cause harmfully high pressures within the eye. The inclusion of regularly spaced pressure sensors 502-510 provides for the measurement and monitoring of pressure along the length of the flexible elongate member 422. Thus, embodiments of the infusion line 422 include one or more internal pressure sensors to provide useful information to a surgeon using the infusion line 420 about the status of the line 420.

FIGS. 5B and 5C are exemplary charts of the pressure as measured by the pressure sensors 502-510 according to their distance along the flexible elongate member 422. As illustrated in FIG. 5B, the x-axis of the chart is the distance along the length of the flexible elongate member 422 and the y-axis is the pressure. The chart illustrates the pressure inside the flexible elongate member at a given time at the positions corresponding to pressure sensors 502-510, with the pressure measured according to the sensor indicated in parentheses. Due to the kink 512, the pressure in the line 420 is higher on the proximal side than on the distal side. Thus, the pressure sensors 502 and 504 measure a significantly higher pressure than the pressure sensors 506, 508, 510 measure. This may be interpreted as indicating the presence and general location of the kink 512.

FIG. 5C is an exemplary chart of the differential pressure calculated from pressure measurements taken by pressure sensors 502-510. Each differential pressure measurement is equal to the difference between a given pressure sensor's measurement and the measurement of the closest, more proximate sensor. Thus, the differential pressure sensor measurement associated with pressure sensor 504 is the pressure as measured by pressure sensor 504 minus the pressure as measured by 502. As illustrated, a significant differential pressure is observed by pressure sensor 506. This pressure reflects the difference from the proximal side of the flexible elongate member 422 to the distal side of the kink 512. This differential pressure may indicate the presence and the general location of the kink 512.

The pressure measurements as presented by FIGS. 5B and 5C may both be used during a surgical procedure. This information may be provided continuously or periodically to a data processor present in console 102 of FIG. 1. The console 102 may be configured to provide visual and/or audio alarms when a kink 512 or flow impediment forms along the length of flexible elongate member 422, enabling the flow problem, which is detected by the pressure sensors, to be resolved before it causes harm to a patient's eye.

Figure 6:
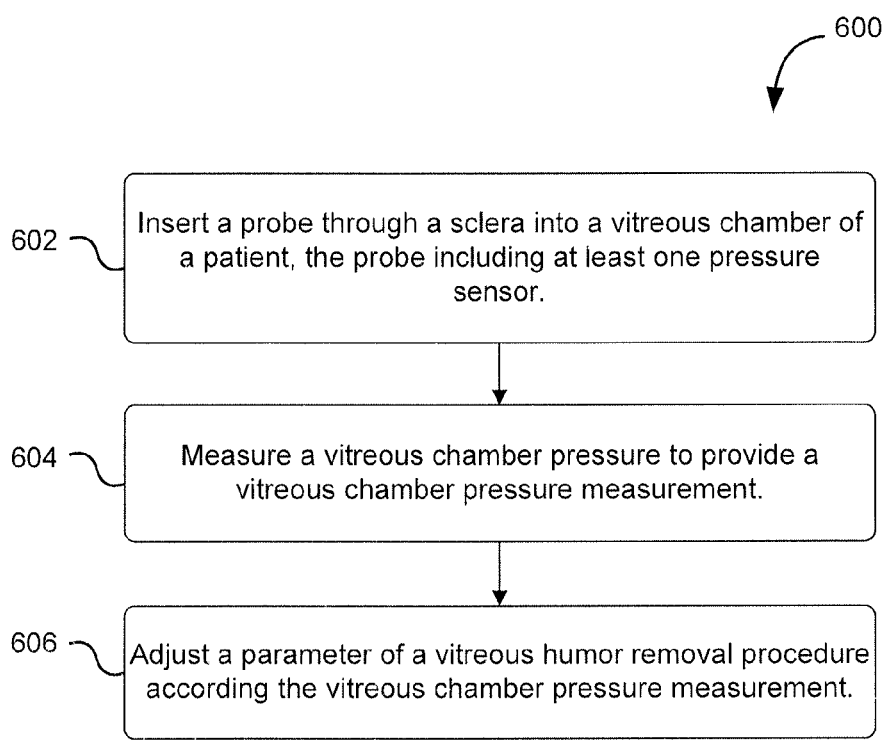
FIG. 6 is a flowchart showing a method of treating an ophthalmic condition according to exemplary aspects of the present disclosure.

FIG. 6 is a flowchart of a method 600 of treating an ophthalmic condition. As illustrated, the method 600 includes a number of enumerated steps, but embodiments of the method 600 may include additional steps before, after, and in between the enumerated steps. The illustrated embodiment begins in step 602 in which a surgeon inserts a probe that includes at least one pressure sensor through a sclera into a vitreous chamber of a patient. In step 604, a vitreous chamber pressure is measured, using the pressure sensor, to provide a vitreous chamber pressure measurement. In step 606, a vitreous humor removal procedure is adjusted according to the vitreous chamber pressure measurement.

In order to better understand the performance of method 600, reference will be made to the systems illustrated in FIGS. 1, 2, 3, 4, and 5A-C and described above. For example, step 602 may be performed when a surgeon inserts the probe system 410 and the infusion line 420. Either or both of these two components, the probe system 410 and the infusion line 420, include at least one pressure sensor for attaining pressure measurements. As illustrated in FIG. 4, the probe system 410 includes three pressure sensors, while the infusion line 420 includes two. Step 604 may be performed by using either or both of the pressure sensors 428 and 414 in order to obtain a pressure measurement or measurements within the vitreous chamber 404. Pressure data obtained from the pressure sensors 428 and/or 414 may be provided to a console 102 configured to process the data. The console 102 communicates the pressure data to the surgeon in order to properly adjust a vitreous humor removal rate according to the measured vitreous chamber pressure, in step 606. In some embodiments, the console 102 may automatically adjust parameters associated with the vitreous humor removal procedure such as a suction pressure and/or a cutter speed. Additionally, the console 102 may automatically adjust the flow of replacement fluid entering the vitreous chamber 404 through the infusion line 420. The flow of a replacement fluid may also be adjusted by the surgeon based on the obtained pressure measurements.

In addition to measuring the vitreous chamber pressure, the various pressure sensors of the probe system 410 and/or the infusion line 420 may be used to measure other pressures including ambient pressures and suction pressures. These additional pressure measurements may be used in calculating a differential pressure, such as intraocular pressure, that may be used as an alternative or in addition to the measured vitreous chamber pressure. Thus, pressure measured at any or all of the locations of the pressure sensors may provide a surgeon or the console 102 with information to monitor and correct the performance of the procedure while it is underway.

The systems and methods disclosed herein may be used to provide better performance of vitrectomy probe system and surgical systems by enabling pressure measurements to be obtained that multiple sites of interest during a surgical procedure. This additional information may enable a surgeon to better tailor parameters such as a removal rate and/or a fluid replacement rate in order to maintain pressures within the vitreous chamber 404 at appropriate levels. Similarly, the pressure information may allow for the automatic adjustment of these rates and others by the console 102. This may result in more effective treatment and more accurate data, thereby improving the overall clinical result.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for providing irrigation into an eye of a patient during a medical procedure, the system comprising:
   an infusion line configured to place a fluid source in fluid communication with the eye of the patient, the infusion line including:
      a flexible elongate member having a proximal end, a distal end, and a lumen extending therethrough from the proximal end to the distal end, the lumen being configured to pass irrigation fluid to the eye of the patient;
      an engagement member at the distal end, the engagement member being more rigid than the flexible elongate member and being configured to enter into a vitreous chamber of the eye of the patient; and
   at least three pressure sensors internally disposed in the infusion line and configured to measure one or more pressures within the infusion line during the medical procedure, wherein the at least three pressure sensors are arranged to detect a pressure differential associated with a flow impediment along the infusion line between two of the at least three pressure sensors, such that the flow impediment is locatable between the two pressure sensors associated with the flow impediment pressure differential.

2. The system of claim 1, further comprising a recess formed in the flexible elongate member, the recess opening into the lumen and containing at least one of the at least three pressure sensors wherein the at least one of the at least three pressure sensors lies flush with the recess to minimize impact on flow through the lumen.

3. The system of claim 2, wherein the at least three pressure sensors are spaced regularly along a portion of a length of the flexible elongate member.

4. The system of claim 1, further comprising a console, the console receiving pressure data from the at least three pressure sensors and is configured to identify the flow impediment along the flexible elongate member based on the pressure data.

5. The system of claim 1, further comprising a fiber-optic coupling element or an electric coupling element disposed at the proximal end of the flexible elongate member.

6. The system of claim 1, wherein an additional first pressure sensor is disposed on an outer surface of the rigid engagement member so as to measure pressure in the vitreous chamber when the rigid engagement member is inserted into the eye.

7. The system of claim 6, wherein an additional second pressure sensor is disposed on an outer surface of the flexible elongate member so as to measure an ambient pressure.

8. The system of claim 1, further comprising a controller configured to receive pressure measurements from the at least three pressure sensors to identify which two pressure sensors have the pressure differential associated with the flow impediment along the infusion line such that the flow impediment is locatable between the two identified pressure sensors.

9. A vitrectomy surgical system comprising:
an infusion line configured to place a fluid source in fluid communication with an eye of a patient,
a vitrectomy probe having a cutting portion comprising an inner cutting tube, an outer cutting tube, and an outer port, the inner cutting tube being movable relative to the outer cutting tube to cut vitreous humor during a vitrectomy procedure, wherein the vitrectomy probe is configured to be moved independently from the infusion line, wherein the infusion line and the vitrectomy probe are configured to be used together to perform a medical procedure;
a motor configured to move the inner cutting tube relative to the outer cutting tube to open and close the outer port;
a first set of three or more pressure sensors coupled to the infusion line wherein the first set of three or more pressure sensors are arranged to detect a pressure differential associated with a flow impediment along the infusion line between two of the three or more pressure sensors, such that the flow impediment is locatable between the two pressure sensors associated with the flow impediment pressure differential; and
a second set of one or more pressure sensors coupled to the vitrectomy probe to measure one or more pressures associated with the vitrectomy probe, wherein a first pressure sensor of the second set of one or more pressure sensors is disposed on an outer surface of the outer cutting tube between the outer port and a probe housing such that the first pressure sensor is configured to measure a vitreous chamber pressure.

10. The system of claim 9, wherein the first pressure sensor of the second set is disposed within a recess formed in the outer cutting tube.

11. The system of claim 9, wherein a second pressure sensor of the second set of one or more pressure sensors is disposed within the inner cutting tube such that the second pressure sensor is configured to measure an aspiration pressure during the vitrectomy procedure.

12. The system of claim 11, wherein the first pressure sensor and the second pressure sensor are used to provide a differential pressure measurement.

13. The system of claim 9, further comprising an ambient pressure sensor coupled to the system to provide a measurement of an atmospheric pressure.

14. The system of claim 9, further comprising a recess formed in the infusion line, the recess opening into a lumen of the infusion line and containing at least one of the three or more pressure sensors wherein the at least one of the three or more pressure sensors lies flush with the recess to minimize impact on flow through the lumen.

15. The system of claim 9,
wherein the infusion line includes:
a flexible elongate member having a proximal end, a distal end, and a lumen extending therethrough from the proximal end to the distal end, the lumen being configured to pass irrigation fluid to the eye of the patient; and
an engagement member at the distal end, the engagement member being more rigid than the flexible elongate member and being configured to enter into a vitreous chamber of the eye of the patient.

16. A method of treating an ophthalmic condition, the method comprising:
inserting a probe through a sclera into a vitreous chamber of an eye of a patient, the probe including at least one pressure sensor;
inserting an infusion line comprising at least three pressure sensors internally disposed in the infusion line, wherein the at least three pressure sensors are arranged to detect a pressure differential associated with a flow impediment along the infusion line between two of the at least three pressure sensors, such that the flow impediment is locatable between the two pressure sensors associated with the flow impediment pressure differential;
measuring a vitreous chamber pressure with the at least one pressure sensor on the probe to provide a vitreous chamber pressure measurement; and
adjusting a parameter of a vitreous humor removal procedure based upon the vitreous chamber pressure measurement.

17. The method of claim 16, further comprising measuring a pressure internal to the probe with the at least one pressure sensor on the probe.

18. The method of claim 16, wherein adjusting a parameter of the vitreous humor removal procedure comprises changing a cutting rate of the vitreous humor removal procedure, changing an irrigation fluid pressure, or changing an aspiration pressure.

19. The method of claim 16, wherein adjusting a parameter of the vitreous humor removal procedure comprises increasing a flow rate of an irrigation fluid.

20. The method of claim 16, comprising determining intraocular pressure of the eye during the vitreous humor removal procedure using a differential pressure that includes the vitreous chamber pressure measurement as one of its components.

* * * * *